US008183176B2

(12) United States Patent
Liu et al.

(10) Patent No.: US 8,183,176 B2
(45) Date of Patent: May 22, 2012

(54) USE OF ADJUVANTS TO IMPROVE ABSCISIC ACID PERFORMANCE

(75) Inventors: Xiaozhong Liu, Vernon Hills, IL (US); Daniel F. Heiman, Libertyville, IL (US); Derek D. Woolard, Zion, IL (US); Rick Hopkins, Fresno, CA (US); Yueh Wang, Arlington Heights, IL (US); Benjamin Belkind, Wilmette, IL (US); Prem Warrior, Green Oaks, IL (US); Gregory D. Venburg, Deerfield, IL (US); Peter D. Petracek, Grayslake, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 0 days.

(21) Appl. No.: 13/110,183

(22) Filed: May 18, 2011

(65) Prior Publication Data
US 2011/0237434 A1    Sep. 29, 2011

Related U.S. Application Data

(63) Continuation of application No. 12/011,820, filed on Jan. 30, 2008, now Pat. No. 7,968,497.

(60) Provisional application No. 60/898,458, filed on Jan. 31, 2007, provisional application No. 60/898,588, filed on Jan. 31, 2007, provisional application No. 60/898,548, filed on Jan. 31, 2007, provisional application No. 60/898,587, filed on Jan. 31, 2007, provisional application No. 60/898,600, filed on Jan. 31, 2007, provisional application No. 60/898,471, filed on Jan. 31, 2007.

(51) Int. Cl.
*A01N 25/00* (2006.01)
(52) U.S. Cl. ............... 504/116.1; 504/101; 71/28
(58) Field of Classification Search .............. 504/116.1, 504/101; 71/28
See application file for complete search history.

(56) References Cited

U.S. PATENT DOCUMENTS

| 4,581,057 A * | 4/1986 | Nooden ................. 71/28 |
| 4,943,315 A * | 7/1990 | Schulz et al. ............ 504/140 |
| 2005/0198896 A1 | 9/2005 | Quaghebeur |

OTHER PUBLICATIONS

Wilen et al. "Effects of Abscisic Acid (ABA) and ABA Analogs on Freezing Tolerance, Low-temperature Growth, and Flowering in Rapeseed", J. of Plant Growth Regul. (1994) 13:235-241.*
Steffens et al. "Selection of Fatty Acid Derivatives- Surfactant Formulations for the Control of Plant Meristems," J. Agr. Food Chem., vol. 17, No. 2; Mar.-Apr. 1969, pp. 312-317.*
Finkelstein et al., "Abscisic acid biosynthesis and response", The *Arabidopsis* Book, American Society of Plant Biologists 2002, pp. 1-52.
Raschke et al., "Simultaneous and independent effects of abscisic acid on stomata and the photosynthetic apparatus in whole leaves", Planta 1985, 163: pp. 105-118.
S. Assmann "D6. Abscisic Acid Signal Transduction in Stomatal Responses", 2004 In: *Plant Hormones Biosynthesis, Signal Transduction, Action* ed. Davies, pp. 391-412.
Downton et al., "Stomatal Closure Fully Accounts for the Inhibition of Photosynthesis by Abscisic Acid", New. Phytol. 1988, 108, pp. 263-266.
Blumenfeld et al., "Cuticular penetration of abscisic acid", May 5, 1972, Planta (Berl.) 107, pp. 261-268.
Cutler et al., "Formation and breakdown of ABA", Trends in Plant Science, Dec. 1999, vol. 4 No. 12, pp. 472-478.
Shulman et al. "Using urea phosphate to enhance the effect of gibberellins $A_3$ on grape size*", Plant Growth Regulation, 1987, 5: pp. 229-234.
Wang et al., "Foliar uptake of pesticides-present status and future challenge", Pesticide Biochemistry and Physiology, 2007, 87 pp. 1-8.
Naito et al. "Effects of the prebloom application of GA combined with BA and urea on the set and growth of seedless berries in Delaware Grapes", J. Japan. Soc. Hort. Sci. 1974, 43(3) pp. 215-223.

* cited by examiner

*Primary Examiner* — Susan McCormick Ewoldt
(74) *Attorney, Agent, or Firm* — Wood, Phillips, Katz, Clark & Mortimer

(57) ABSTRACT

This invention relates to the use of selected adjuvants to improve the performance of S-(+)-abscisic acid (S-ABA, ABA) or ABA salts on plants.

9 Claims, No Drawings

USE OF ADJUVANTS TO IMPROVE ABSCISIC ACID PERFORMANCE

RELATED APPLICATIONS

This application is a continuation of U.S. application Ser. No. 12/011,820, filed Jan. 30, 2008, which claims the benefit of U.S. Provisional application Ser. Nos. 60/898,458, 60/898,588, 60/898,548, 60/898,587, 60/898,600, 60/898,471 all filed Jan. 31, 2007. The entire teachings of the above-referenced application is incorporated herein by reference.

FIELD OF THE INVENTION

The present invention relates to the use of selected adjuvants or nitrogen containing fertilizer to improve the performance of abscisic acid (ABA) or its salts thereof by increasing the extent and/or extending the duration of desired biological activity.

BACKGROUND OF THE INVENTION

Abscisic acid (ABA) is a natural occurring hormone found in all higher plants (Cutler and Krochko 1999, Trends in Plant Science, 4:472-478; Finkelstein and Rock 2002, The Arabidopsis Book, ASPB, Monona, Md., 1-52). ABA is involved in many major processes during plant growth and development including dormancy, germination, bud break, flowering, fruit set, general growth and development, stress tolerance, ripening, maturation, organ abscission, and senescence. ABA also plays an important role in plant tolerance to environmental stresses, such as drought, cold, and excessive salinity.

One key role of ABA in regulating physiological responses of plants is to act as a signal of reduced water availability to reduce water loss, inhibit growth and induce adaptive responses. All these functions are related to stomatal closure (Raschke and Hedrich 1985, Planta, 163: 105-118). When stomata close, plants conserve water to survive environmental stresses. However, stomatal closure also can result in reduced photosynthesis, respiration and growth. Stomatal closure is a rapid response of plants to ABA. The mechanism of this effect has been studied and has been shown to be due primarily to ABA effects on guard cell ion channels. Specifically, ABA blocks $H^+$ extrusion and $K^+$ influx from guard cells and promotes $K^+$, $Cl^-$, and malate extrusion and $Ca^{2+}$ influx. The net effect of ABA is to reduce the total osmotica in the guard cells, which in turn decreases the water content in the cell. This causes the guard cells to lose turgor and thus close the stomata (Assmann 2004, In: *Plant Hormones Biosynthesis, Signal Transduction, Action*, ed. Davies, p 391-412). The closing of the stomata results in reduced transpiration. The reduction of transpiration caused by stomatal closure is widely used as an experimental technique to indirectly identify and quantify ABA activity. The ability of ABA to reduce water use can not only extend the display shelf life of ornamentals or the postharvest shelf life of leafy plants, or promote drought tolerance, but it also can lead to a reduction in cold stress injury (Aroca et al. 2003, Plant Sci., 165: 671-679). ABA-induced reduction of stomatal conductance can lead to a decrease in photosynthesis (Downton et al. 1988 New Phytol., 108: 263-266) which in turn can lead to growth control. Improving the performance of ABA may be useful not only for improving the reduction of transpiration and water loss, but also for other uses of foliar applied ABA such as maintaining dormancy of buds and seeds, controlling fruit set, accelerating defoliation, and enhancing color development of fruit such as grapes.

Surfactants or adjuvants have long been used with pesticides and plant growth regulators to increase the absorption or uptake by plants and thus improve the performance of the applied chemicals. Adjuvants include wetter-spreaders, stickers, penetrants, compatibility agents and fertilizers. However, there is little prior art information about adjuvant effects on ABA efficacy. In the patent application of Quaghebeur (2005, US20050198896 A1) it is noted that "ethoxylated sorbitan esters and siloxanes have proved to be particularly suitable for the application of ABA", but there is no mention of adjuvant effects on ABA efficacy. Lee et al. (1997, Kor. Soc. Hort. Sci. J., 38:717-721) reported that the addition of 0.05% Tween 20 (a commercially available ethoxylated sorbitan ester) improved ABA effect. However, Tween 20 is used for academic research and not packaged and distributed for the agricultural market.

The pH of an exogenously applied ABA solution may play a role in determining the efficiency of ABA uptake by plants. At an acidic pH, ABA is in its neutral undissociated form. This form is more lipophilic, and its penetration of the plant cuticle would be favored relative to the charged, dissociated form of ABA present at higher pHs (Blumenfeld and Bukovac 1972, Planta, 107:261-268). The uncharged undissociated form of ABA would more easily cross cell membranes from the relatively acidic apoplast into the cytosol.

Foliar applied nitrogen fertilizers, such as urea or ammonium nitrate, have been used in combination with plant growth regulators (PGRs) to improve the performance of the PGR. For example, the combination of the PGRs benzyladenine (Naito et al. 1974, J. Japan. Soc. Hort. Sci., 43: 215-223) or gibberellic acid (Shulman et al. 1987, Plant Growth Regul., 5: 229-234) with urea increased the grape berry sizing effect compared to the sizing effect achieved with the PGR alone. Ammonium salts have been reported to increase the absorption of pesticides (Wang and Liu 2007, Pestic. Biochem., Physiol., 87: 1-8). Nooden (1986, U.S. Pat. No. 4,581,057) claims the use of ABA to increase fertilizer performance. However, there are no reports of the use of urea ($H_2NCONH_2$) or ammonium nitrate ($NH_4NO_3$) to improve ABA performance.

In order maximize the performance of ABA in its various agricultural and horticultural applications; there is a need to improve the extent and duration of ABA efficacy.

SUMMARY OF THE INVENTION

The present invention is directed toward the incorporation of an effective amount of an adjuvant selected from the group consisting of polyoxyethylene fatty alcohol ethers, nonylphenyl ethoxylates and phthalic/glycol alkyl resins into an ABA or ABA salt-containing end-use solution composition or into a liquid or solid formulation composition intended for preparation of such an end-use solution in order to increase the effectiveness of ABA by increasing the extent and/or extending the duration of its desired biological activity. This is then accomplished by applying said end-use solution composition directly to target plants or the locus thereof by spraying or drenching.

The present invention is also directed to the incorporation of an effective amount of an adjuvant selected from the group consisting of polyoxyethylene fatty alcohol ethers, nonylphenyl ethoxylates and phthalic/glycol alkyl resins into an ABA or ABA salt-containing end-use solution composition in order to decrease the ABA application rate required to attain a targeted degree or duration of ABA biological activity.

The present invention is also directed to the incorporation of an effective amount of an adjuvant selected from the group consisting of polyoxyethylene fatty alcohol ethers, nonylphenyl ethoxylates and phthalic/glycol alkyl resins into an ABA or ABA salt-containing in bottle formulation in order to decrease the ABA application rate required to attain a targeted degree or duration of ABA biological activity.

The presently preferred polyoxyethylene fatty alcohol ethers useful in the present invention are members of the Brij family of surfactants. The most preferred member of the Brij family of surfactants is Brij 98 (polyoxyethylene (20) oleyl ether).

A presently preferred nonylphenol ethoxylate is Agral 90.

A presently preferred phthalic/glycol alkyl resin is Latron B 1956.

The present invention is also directed to the incorporation of an effective amount of Brij 98 (polyoxyethylene (20) oleyl ether) and a nitrogen containing fertilizer, such as urea into an ABA-containing end-use solution or formulation that is diluted to produce an end-use solution, and to the application of said solution to a plant or plants or to the locus of a plant or plants.

DETAILED DESCRIPTION OF THE INVENTION

The compositions of the present invention improve ABA effectiveness by incorporating a surfactant, and optionally a nitrogen-containing fertilizer together with an effective amount of the plant growth regulator abscisic acid (S-ABA; ABA; S-(+)-abscisic acid; +-ABA, (+)-(S)-cis,trans-abscisic acid, (+)-(S)-cis,trans-ABA; S-ABA; (S)-5-(1-hydroxy-2,6,6, -trimethyl-4-oxo-2-cyclohexen-1-yl)-3-methyl-(2Z,4E)-pentadienoic acid; CAS registry no. [21293-29-8]). ABA effectiveness may be measured experimentally by quantifying the inhibition of transpiration in tomato leaves. This is a reliable laboratory bioassay of the level of ABA activity.

The compositions of the present invention comprise ABA or a salt thereof, together with a polyoxyethylene fatty alcohol ether, nonylphenol ethoxylate or phthalic/glycol alkyl resin adjuvant, and may be used to form to a ready-to-apply liquid solution, a mixture prepared by the end user of the ABA or a solid or liquid formulation concentrate. The effectiveness of the compositions of the present invention was demonstrated by tomato leaf transpiration inhibition. The response of tomato plants to ABA is representative of the response of other plant species, such as nursery plants, to ABA. Other physiological processes regulated by ABA such as the promotion of drought tolerance of bedding plants, fruit coloration, dormancy of buds and seeds, plant growth control, defoliation, and chilling and freeze stress protection are expected to respond to the combinations of ABA or ABA salts with adjuvants of this invention.

The presently preferred surfactants for incorporation into the ABA compositions of the present invention are members of the Brij family (polyoxyethylene fatty alcohol ethers), available from Uniqema (Castle, Del.), including Brij 58 (polyoxyethylene (20) cetyl ether), Brij 76 (polyoxyethylene (10) stearyl ether), Brij 78 (polyoxyethylene (20) stearyl ether), Brij 98 (polyoxyethylene (20) oleyl ether) and Brij 700 (polyoxyethylene(100) stearyl ether); Agral 90 (Nonylphenol ethoxylate) available from Norac Concept. Inc. (Orleans, Ontario, Canada) and Latron B-1956 (77.0% modified phthalic/glycerol alkyl resin and 23.0% Butyl alcohol) available from Rohm & Haas (Philadelphia, Pa.). The presently most preferred surfactant for incorporation into the ABA compositions of the present invention is Brij 98 (polyoxyethylene (20) oleyl ether), optionally in combination with nitrogen-containing fertilizers or other adjuvants.

The presently preferred combination of nonionic surfactant and anionic wetting agent for improving ABA performance is Brij 98 plus Monawet MO-84R2W (84% sodium dioctyl sulfosuccinate anionic wetting agent in propylene glycol solvent) in a suitable solvent such as ethyl lactate.

The presently preferred combination of surfactant and nitrogen-containing fertilizer for improving ABA performance is Brij 98 and urea.

As used herein, the term "salt" refers to the water soluble salts of ABA or ABA analogs or derivatives, as appropriate. Representative such salts include inorganic salts such as the ammonium, lithium, sodium, potassium, calcium and magnesium salts and organic amine salts such as the triethanolamine, dimethylethanolamine and ethanolamine salts.

Depending on the target plant species, physiological processes of interest, and environmental conditions, the effective concentration of ABA can vary, but it is generally in the range of about 0.1 ppm to about 10,000 ppm, and preferably from about 1 to about 1000 ppm.

The preferred concentration of nonionic surfactant or/and anionic wetting agent surfactant in the end-use solutions of the present invention is about 0.001% to about 25% w/v, preferably from about 0.01% to about 5.0%.

Thus, a presently preferred composition of the present invention comprises from about 0.1 ppm to about 10,000 ppm ABA, from about 0.05 to about 5.0% weight of a surfactant or/and wetting agent, optionally from about 0.1 mM to about 1000 mM of a nitrogen-containing fertilizer, with the balance of the composition consisting of water.

The effective concentration range of ABA depends on the water volume applied to plants as well as other factors such the plant age and size, the plant species and varietal sensitivity to ABA, and the targeted physiological process.

The invention is illustrated by, but is not limited by, the following representative examples.

EXAMPLES

Preparation of plant specimens for use in the treatment studies of the examples described was carried out as follows. Tomato (variety: Rutgers) seeds were sown in an 18-cell flat filled with Promix PGX (available from Premier Horticulture Inc. Quakertown, Pa.) and grown for 3 weeks to allow for germination and initial growth. Plants were then transplanted into pots (18 cm in diameter and 18 cm in height), filled with Promix BX (available from Premier Horticulture Inc. Quakertown, Pa.), and grown for one or two more weeks before treatment, depending on temperature and available light. Plants received daily irrigation and weekly fertilizer (1 g/L all purpose fertilizer 20-20-20, available from The Scotts Company, Marysville, Ohio).

All treatment solutions were prepared with distilled water. ABA (95% active ingredient) is available from Lomon Bio-Technology Co., Ltd. (Shichuan, China). Twenty L of 250 ppm ABA solution was prepared and stored in the dark at 20-25° C. This 250-ppm ABA solution was used for all studies to eliminate the possibility of applying an incorrect concentration of ABA.

Brij 98, Monawet MO-84R2W, Tween 20 and Tween 60 are available from Uniqema (New Castle, Del.). Ethyl lactate used to solubilize Brij 98 is available from Fluka Chemie GmbH (Buchs, Germany). Silwet L-77 is available from GE Silcones (Wilton, Conn.).

Agral 90 is available from Norac Concept. Inc. (Orleans, Ontario, Canada).

Latron B-1956 is available from Rohm & Haas (Philadelphia, Pa.).

Unless otherwise specified, when a surfactant was employed, it was incorporated into the 250-ppm ABA treatment solution at a concentration of 0.05% to 0.5% (v/v).

ABA solutions and blank treatments were applied to the aerial parts of tomato plant leaves at the rate of 20 mL per 6 plants. Plants were then placed in a transparent chamber with humidity controlled within the range of 40 to 60% relative humidity. Leaf transpiration rates were measured at 1, 2 and 3 days; at 1, 2, 3 and 4 days; or at 1, 2, 3, 4 and 7 days after treatment. Measurements were conducted using a LI-1600 Steady State Porometer (LI-Cor, Lincoln, Neb.). Each day the transpiration rate of the plants of each treatment group was normalized to the percentage of the transpiration rate of untreated plants (plants sprayed with water only) in order to control for day-to-day variability caused by changes of environmental conditions such as light intensity and temperature. In some cases, data of each plant was averaged over a 3-day period to balance the short term and long-term effect of ABA on tomato leaf transpiration as well as to control for experimental variability.

A grape coloring field study was conducted at Caruthers, Calif. ABA alone at 100 or 200 ppm or its combination with 0.05% Brij 98 was foliar applied to Crimson seedless grapes. Number of clusters with color was counted on a weekly basis, beginning at 21 days after treatment. Percentage of clusters with color was calculated. Grape yield was harvested at 64 days after treatment.

A grape coloring field study was conducted at Caruthers, Calif. ABA alone at 100 or 200 ppm or its combination with 0.05% Latron B-1956 was foliar applied to Crimson seedless grapes. Number of clusters with color was counted on a weekly basis, beginning at 21 days after treatment. Percentage of clusters with color was calculated. Grape yield was harvested at 64 days after treatment.

All experiments were conducted using a randomized complete block experimental design. Data were analyzed by analysis of variance. Duncan's new multiple range tests at $\alpha=0.05$ were used for mean separations.

Example 1

Tomato plants treated with various concentrations of ABA alone or in combination with 0.05% Brij 98 were studied (Table 1). ABA alone significantly reduced tomato leaf transpiration when applied at 250, 500 and 1000 ppm, but not at 125 ppm over the 3-day period. Transpiration inhibition increased with increasing ABA concentrations. Transpiration inhibition from the ABA application was greater when the ABA was applied with 0.05% Brij 98 compared to the same ABA concentration applied without adjuvant.

The relationship between relative transpiration and the base-10 logarithm of ABA concentration was linear with or without 0.05% Brij 98 (Table 1). ABA concentrations for 50% inhibition of transpiration were calculated to be 3328 ppm without Brij 98 and 191 ppm with 0.05% Brij 98. These results demonstrate that the addition of Brij 98 surfactant increases ABA performance as measured by the tomato leaf transpiration inhibition bioassay.

TABLE 1

The relationship between applied ABA concentration and tomato leaf transpiration with or without 0.05% Brij 98

| ABA Concentration (ppm) | $Log_{10}$ [ABA] | Transpiration rate (% of control) | |
|---|---|---|---|
| | | without 0.05% Brij 98 | with 0.05% Brij 98 |
| 0 | | 100 | 103 |
| 125 | 2.1 | 96 | 58 |
| 250 | 2.4 | 88 | 45 |
| 500 | 2.7 | 74 | 32 |
| 1000 | 3.0 | 68 | 25 |
| Equation* | | y = 164 − 32 x | y = 134 − 37 x |
| $R^2$ | | 0.98 | 0.98 |
| ABA concentrations to achieve 50% inhibition of transpiration | | 3328 ppm | 191 ppm |

*In this equation, y is the relative transpiration (% of control) of the average value of first 3 days after treatment; x is the base 10 logarithm of ABA concentration.

Example 2

The effect of varying Brij 98 concentrations on the efficacy of 250-ppm ABA treatment was examined (Table 2). The addition of Brij 98 significantly improved ABA performance. The transpiration rate decreased with the increasing concentrations of Brij 98. Transpiration inhibition lasted longer at higher concentrations of Brij compared to that achieved with lower concentrations Brij 98. Results demonstrate that a higher concentration of Brij 98 applied with ABA improves ABA performance as compared to a lower concentration of Brij 98.

TABLE 2

Effect of varying the concentration of Brij 98 on ABA performance as measured in the tomato leaf transpiration inhibition bioassay.

| Treatment | Transpiration rate (% of control) Days after treatment | | |
|---|---|---|---|
|  | 1 | 2 | 3 |
| Control | 100 | 100 | 100 |
| 250 ppm ABA | 76 | 99 | 93 |
| 250 ppm ABA + 0.01% Brij 98 | 54 | 97 | 99 |
| 250 ppm ABA + 0.05% Brij 98 | 25 | 56 | 67 |
| 250 ppm ABA + 0.10% Brij 98 | 16 | 41 | 49 |
| 250 ppm ABA + 0.50% Brij 98 | 7 | 32 | 46 |

Example 3

The effect of 0.05% Tween 60 to improve ABA performance was examined and compared to the effect of 0.05% Brij 98 to improve ABA performance (Table 3). Both 0.05% Tween 60 and 0.05% Brij 98 significantly improved ABA performance as measured by the tomato leaf transpiration inhibition bioassay. However, the transpiration rates of plants treated with ABA alone and plants treated with ABA plus Tween 60 were much higher than the transpiration rates of plants treated with ABA plus Brij 98. These results demonstrate that Brij 98 is much more effective than Tween 60 in improving ABA performance for leaf transpiration inhibition.

TABLE 3

Comparison between Brij 98 and Tween 60 for improving ABA inhibition of tomato leaf transpiration.

| Treatment | Transpiration rate (% of control) |
|---|---|
| Control | 100 |
| 250 ppm ABA | 83 |
| 250 ppm ABA + 0.05% Brij 98 | 32 |
| 250 ppm ABA + 0.05% Tween 60 | 69 |

Data listed in the table was the average value of first 3 days after treatment.

Example 4

The effect of 0.05% Silwet L-77 to improve ABA performance was examined and compared to the effect of 0.05% Brij 98 to improve ABA performance (Table 4). Both 0.05% Silwet L-77 and 0.05% Brij 98 significantly improved ABA performance as measured by the tomato leaf transpiration inhibition bioassay. However, the transpiration rates of plants treated with either ABA alone or with ABA plus Silwet L-77 were much higher than those of plants treated with ABA plus Brij 98. Results indicate that Brij 98 is much more effective in improving ABA performance than Silwet L-77.

TABLE 4

Comparison between Brij 98 and Silwet L-77 to improve ABA inhibition as measured by the tomato leaf transpiration inhibition bioassay.

| Treatment | Transpiration rate (% of control) |
|---|---|
| Control | 100.02 |
| 250 ppm ABA | 96.32 |
| 250 ppm ABA + 0.05% Brij 98 | 41.23 |
| 250 ppm ABA + 0.05% Silwet L-77 | 64.25 |

Data listed in the table was the average value of first 3 days after treatment.

Example 5

Three Brij family surfactants with the same polyoxyethylene oligomer length, Brij 58, Brij 78, and Brij 98 were tested for their effect on ABA performance as measured by the tomato leaf transpiration inhibition bioassay (Table 5). Each of the three surfactants was tested at 0.05% and 0.5% concentrations. Brij 58, Brij 78 and Brij 98 at either concentration significantly improved ABA performance. For each surfactant, ABA applied with the higher surfactant concentration was more effective than ABA applied with the lower surfactant concentration. Of the three surfactants, Brij 98 improved ABA performance best.

TABLE 5

Comparison of surfactants in Brij family having the same polyoxyethylene tail length for improvement of ABA performance as measured by inhibition of tomato leaf transpiration

| Treatment | Transpiration rate (% of control) Days after treatment | | | |
|---|---|---|---|---|
|  | 1 | 2 | 3 | 4 |
| Control | 100 | 100 | 100 | 100 |
| 250 ppm ABA | 82 | 91 | 90 | 100 |
| 250 ppm ABA + 0.05% Brij 58 | 44 | 47 | 60 | 99 |
| 250 ppm ABA + 0.50% Brij 58 | 29 | 44 | 45 | 70 |
| 250 ppm ABA + 0.05% Brij 78 | 39 | 44 | 53 | 97 |
| 250 ppm ABA + 0.50% Brij 78 | 22 | 42 | 46 | 75 |
| 250 ppm ABA + 0.05% Brij 98 | 36 | 41 | 52 | 74 |
| 250 ppm ABA + 0.50% Brij 98 | 24 | 28 | 41 | 51 |

Example 6

Brij 76 was examined and compared to Brij 98 for its effect on ABA performance as measured by inhibition of tomato leaf transpiration (Table 6). Inclusion of Brij 76 at 0.05% or 0.5% significantly improved ABA performance. ABA applied with 0.5% Brij reduced transpiration more than ABA applied with 0.05% Brij 76 did. At the same ABA concentration, ABA applied in conjunction with Brij 98 was more effective than ABA applied with Brij 76.

TABLE 6

Comparison of two Brij surfactants for improvement of ABA performance as measured by inhibition of tomato leaf transpiration.

| Treatment | Transpiration rate (% of control) Days after treatment | | | |
|---|---|---|---|---|
| | 1 | 2 | 3 | 4 |
| Control | 100 | 100 | 100 | 100 |
| 250 ppm ABA | 71 | 84 | 86 | 90 |
| 250 ppm ABA + 0.05% Brij 98 | 27 | 43 | 53 | 64 |
| 250 ppm ABA + 0.05% Brij 76 | 33 | 43 | 66 | 72 |
| 250 ppm ABA + 0.50% Brij 76 | 29 | 29 | 45 | 54 |

Example 7

Preparation of an aqueous solution composition of the ammonium salt of (S)-(+)-abscisic acid comprising potassium sorbate In a 600 mL beaker, 55 g of (S)-(+)-abscisic acid of 95% purity was added, followed by 500 µL of Tween 20 and 200 mL of water. Then, 10 mL of concentrated aqueous ammonia was added with stirring until the mixture came to equilibrium. Then, additional concentrated ammonia was added dropwise until all the solid was dissolved. A homogenous solution was achieved when a total of about 13.5 mL of ammonia has been added. At this point, potassium sorbate (1.25 g) was added to the composition; it quickly dissolved. The mixture was transferred to a 500 ml volumetric flask and was brought up to 500 mL total volume with deionized water. The mixture was stored in a brown glass bottle. The pH was measured to be 6.50.

An aqueous solution composition comprising 10% abscisic acid as the ammonium salt by weight, and further comprising a naturally-occurring antimicrobial preservative, was prepared.

Example 8

Preparation an aqueous solution composition of the ammonium salt of (S)-(+)-abscisic acid comprising Brij 98 surfactant).

A solution was prepared containing 5.0 g of Brij 98 in approximately 20 mL of water. (S)-(+)-abscisic acid (2.64 g of 95% purity) was added, followed by the theoretical amount of ammonia as the commercial concentrated aqueous solution. All of the abscisic acid quickly dissolved. Preservative (63 mg of potassium sorbate) was added, and it quickly dissolved. The pH of the resulting clear solution was 6.92. It was made up to a final volume of 50 mL to give a concentration of 5% abscisic acid as the ammonium salt and 10% Brij 98 by weight.

An aqueous solution composition comprising 5% abscisic acid by weight as the ammonium salt and further comprising a high concentration of Brij 98 surfactant was prepared.

Example 9

The difference between ABA and ABA ammonium salt was compared with or without 0.05% Brij 98 (Table 7). Both ABA and its ammonium salt at 250 ppm concentration decreased the transpiration rate. The addition of 0.05% Brij 98 into ABA or its ammonium salt significantly improved their performance. The transpiration rate was higher for ABA with or without Brij 98 than ABA ammonium salt with or without Brij 98.

TABLE 7

Effect of Brij 98 on improving performance of ABA or ABA ammonium salt for tomato leaf transpiration inhibition.

| Treatment | Transpiration rate (% of control) Days after treatment | | | |
|---|---|---|---|---|
| | 1 | 2 | 3 | Average |
| Control | 100 | 100 | 100 | 100 |
| 250 ppm ABA | 73 | 76 | 94 | 81 |
| 250 ppm ABA + 0.05% Brij 98 | 25 | 39 | 42 | 35 |
| 250 ppm ABA ammonium salt | 68 | 73 | 84 | 75 |
| 250 ppm ABA ammonium salt + Brij 98 | 17 | 19 | 32 | 23 |

Example 10

Preparation of an aqueous solution composition of the triethanolamine salt of (S)-(+)-abscisic acid comprising a high concentration of Brij 98 surfactant To a solution of 50 mg Tween 20 in 10 mL of water was added 2.64 g of (S)-(+)-abscisic acid (10 mmoles of 95% purity). Triethanolamine (1.33 mL, 10 mmoles) was added dropwise with good stirring, resulting in a clear, homogeneous solution. This solution was heated to 55° C., and Brij 98, liquified by warming in a 55° C. oven, was added. After stirring to achieve a homogeneous solution, the mixture was diluted with additional water to a final volume of 25 mL.

An aqueous solution composition comprising 10% abscisic acid by weight as the triethanolamine salt and further comprising 20% by weight Brij 98 as a performance enhancing additive was prepared.

Example 11

The effect of ABA triethanolamine salt with Brij 98 on tomato leaf transpiration was studied (Table 8). ABA triethanolamine salt at a rate equivalent to 250 ppm ABA applied together with Brij 98 significantly improved ABA performance. The result demonstrates that Brij 98 incorporated into a treatment can improve ABA salt performance for transpiration inhibition.

TABLE 8

Effect of ABA triethanolamine salt with Brij 98 on tomato leaf transpiration.

| Treatment | Transpiration rate (% of control) Days after treatment | | | |
|---|---|---|---|---|
| | 1 | 2 | 3 | Average |
| Control | 100 | 100 | 100 | 100 |
| 250 ppm ABA | 71 | 75 | 88 | 78 |
| 250 ppm ABA triethanolamine salt + Brij 98 | 29 | 28 | 39 | 32 |

Example 12

Brij 98 at 0.05% and the combination of 0.05% Brij 98 with 10 or 100 mM urea were examined for improvement of ABA performance (Table 9). ABA applied with Brij 98 and ABA applied with Brij 98 in combination with 10 or 100 mM urea significantly improved ABA performance as measured by tomato leaf transpiration inhibition over a 3-day period. The addition of urea to Brij 98 plus ABA solution provided more transpiration inhibition than ABA applied in conjunction with Brij 98. Inclusion of a high concentration of urea showed a similar effect as the low concentration of urea. Results demonstrate that Brij 98 and urea have positive effects on ABA performance.

TABLE 9

Effect of Brij 98 or Brij 98 plus urea on ABA performance as measured by tomato leaf transpiration inhibition.

| Treatment | Transpiration rate (% of control) |
|---|---|
| Control | 100 |
| 250 ppm ABA | 73 |
| 250 ppm ABA + 0.05% Brij 98 | 34 |
| 250 ppm ABA + 10 mM Urea + 0.05% Brij 98 | 28 |
| 250 ppm ABA + 100 mM Urea + 0.05% Brij 98 | 27 |

Data listed in the table was the average value of first 3 days after treatment.

Example 13

Preparation of an aqueous solution composition of the ammonium salt of (S)-(+)-abscisic acid comprising Brij 98 surfactant and urea A solution of Brij 98 (5.0 g) was prepared in 10 mL warm water. Adding 2.64 g of (S)-(+)-abscisic acid (10 mmoles of 95% purity) and stirring produced a milky suspension. Adding the theoretical amount of concentrated aqueous ammonia caused the abscisic acid to dissolve quickly. Urea (6.01 g, 100 mmoles) dissolved quickly when added. The solution was made up to a final volume of 25 mL by addition of deionized water.

An aqueous solution composition comprising 10% abscisic acid by weight as the ammonium salt and further comprising both 20% by weight Brij 98 and 24% urea as performance enhancing additives was prepared.

Example 14

Preparation of an aqueous solution composition of the ammonium salt of (5)-(+)-abscisic acid comprising Brij 700 surfactant Brij 700 (5.0 g) was dissolved in 25 mL of water with the aid of heat and stirring. (S)-(+)-abscisic acid (2.64 g of 95% purity) was added, followed by the theoretical amount of ammonia as the commercial concentrated aqueous solution. All of the abscisic acid quickly dissolved. Antimicrobial preservative (63 mg of potassium sorbate) was added, and it quickly dissolved. The resulting solution was made up to 50 mL by addition of deionized water.

An aqueous solution composition comprising 5% abscisic acid by weight as the ammonium salt and further comprising a high concentration of Brij 700 surfactant was prepared.

Example 15

The effect of ABA ammonium salt+Brij 98+Urea and ABA ammonium salt+Brij 700 at rates equivalent to 250 ppm ABA on tomato transpiration was studied (Table 10). The combination of ABA ammonium salt+Brij 98+Urea decreased transpiration much more effectively than ABA alone or ABA ammonium salt only. The combination of ABA ammonium salt+Brij 98+Urea also decreased transpiration more effectively than 250 ppm ABA with 0.05% Brij 98 except on the first day after treatment. The combination of ABA ammonium salt+Brij 700 decreased transpiration more than ABA or ABA ammonium salt alone. However, the combination of ABA ammonium salt+Brij 700 decreased transpiration less than ABA plus 0.05% Brij 98. These results demonstrate that the incorporation of Brij or the combination of Brij 98 with urea in a treatment with ABA salt improved ABA performance for transpiration inhibition.

TABLE 10

Effect of Brij alone or its combination with urea on improving ABA ammonium salt performance for tomato leaf transpiration inhibition

| | Transpiration rate (% of control) Days after treatment | | | |
|---|---|---|---|---|
| Treatment | 1 | 2 | 3 | Average |
| Control | 100 | 100 | 100 | 100 |
| 250 ppm ABA | 59 | 71 | 77 | 69 |
| 250 ppm ABA + 0.05% Brij 98 | 10 | 29 | 38 | 25 |
| 250 ppm ABA ammonium salt | 58 | 67 | 78 | 68 |
| 250 ppm ABA ammonium salt + Brij 98 + Urea | 15 | 28 | 28 | 24 |
| 250 ppm ABA ammonium salt + Brij 700 | 19 | 37 | 47 | 34 |

Example 16

The combination of two adjuvants, 0.04% Brij 98 with 0.01% Monawet MO-84R2W, was compared to 0.05% Brij 98 on improving ABA performance for transpiration inhibition (Table 11). The addition of 0.05% Brij 98 or 0.04% Brij 98 with 0.01% Monawet MO-84R2W into 250 ppm ABA significantly decreased the transpiration rate more than 250 ppm ABA alone. However, there was no significant difference between 0.05% Brij 98 and 0.04% Brij 98 with 0.01% Monawet MO-84R2W on improving ABA performance for transpiration inhibition over a 3-day period. These results demonstrate that the combination of Brij 98 with another type of adjuvant such as wetting agent Monawet MO-84R2W had similar effects to those produced by Brij 98 at 40-60% relative humidity. This combination may have advantage over Brij 98 alone at low humidity conditions.

TABLE 11

Effect of Brij 98 alone or its combination with Monawet MO-84R2W on improving ABA performance for tomato transpiration inhibition.

| | Transpiration rate (% of control) Days after treatment | | | |
|---|---|---|---|---|
| Treatment | 1 | 2 | 3 | Average |
| Control | 100 | 100 | 100 | 100 |
| 250 ppm ABA | 83 | 85 | 94 | 87 |
| 250 ppm ABA + 0.05% Brij 98 | 25 | 33 | 47 | 35 |
| 250 ppm ABA + 0.04% Brij 98 + 0.01% Monawet MO-84R2W | 34 | 41 | 40 | 38 |

Example 17

The effect of 0.05% Brij 98 on ABA (100 or 200 ppm) performance in grape coloration was examined in the field (Table 12). Addition of Brij 98 increased the percent of clusters with color for ABA at 100 or 200 ppm after application and increased the harvest yield percent with sufficient color. Treatment with 200 ppm ABA had more colored clusters and yield.

TABLE 12

Effect of Brij 98 on improving ABA performance in Crimson Seedless grape coloration.

| Treatment | Days after application (% clusters with color) | | | | | | | | Harvest yield (%) |
|---|---|---|---|---|---|---|---|---|---|
| | 21 | 27 | 35 | 43 | 50 | 56 | 62 | 64 | |
| Untreated control | 0.2 | 0.6 | 1.9 | 4.5 | 4.5 | 10.5 | 10.5 | 14.3 | 8.1 |
| ABA (100 ppm) | 1.8 | 2.7 | 5.7 | 7.5 | 9.4 | 26.1 | 26.2 | 31.2 | 25.5 |
| ABA (200 ppm) | 7.0 | 10.7 | 17.3 | 20.5 | 22.7 | 47.9 | 50.3 | 56.4 | 49.1 |
| Brij 98 (0.05%) + 100 ppm ABA | 2.0 | 5.0 | 9.6 | 14.6 | 18.2 | 31.6 | 36.8 | 39.3 | 30.3 |
| Brij 98 (0.05%) + 200 ppm ABA | 14.6 | 16.4 | 23.7 | 30.1 | 34.5 | 58.4 | 60.6 | 71.7 | 61.4 |

Example 18

The efficacy of 0.05% or 0.5% Agral 90 for improvement of ABA performance was examined (Table 13). Agral 90 at either 0.05% or 0.5% concentration significantly improved ABA performance as measured by transpiration inhibition. Agral 90 at 0.5% with 250 ppm ABA caused lower transpiration rate than 0.05% Agral 90 with 250 ppm ABA. These results demonstrate that the commercially available surfactant Agral 90 can be used as an effective surfactant to improve ABA performance.

TABLE 13

Effect of Agral 90 to improve ABA performance as measured by inhibition of transpiration in tomato leaf

| Treatment | Transpiration rate (% of control) Days after treatment | | | |
|---|---|---|---|---|
| | 1 | 2 | 3 | 4 |
| Control | 100 | 100 | 100 | 100 |
| 250 ppm ABA | 74 | 82 | 95 | 100 |
| 250 ppm ABA + 0.05% Agral 90 | 36 | 45 | 57 | 75 |
| 250 ppm ABA + 0.50% Agral 90 | 9 | 38 | 36 | 51 |

Example 19

The efficacy of 0.05% or 0.5% Latron B-1956 for improvement of ABA performance was examined (Table 14). Latron B-1956 at either 0.05% or 0.5% concentration significantly improved. ABA performance as measured by transpiration inhibition. Latron B-1956 at 0.5% with 250 ppm ABA reduced the transpiration rate more effectively than 0.05% Latron B-1956 with 250 ppm ABA. These results demonstrate that the commercially available surfactant Latron B-1956 can be used to improve ABA performance.

TABLE 14

Effect of Latron B-1956 to improve ABA performance as measured by inhibition of tomato leaf transpiration

| Treatment | Transpiration rate (% of control) Days after treatment | | | |
|---|---|---|---|---|
| | 1 | 2 | 3 | 4 |
| Control | 100 | 100 | 100 | 100 |
| 250 ppm ABA | 74 | 82 | 95 | 100 |
| 250 ppm ABA + 0.05% Latron B-1956 | 49 | 53 | 59 | 72 |
| 250 ppm ABA + 0.50% Latron B-1956 | 41 | 47 | 46 | 63 |

Example 20

The effect of 0.05% Latron B-1956 on ABA (100 or 200 ppm) performance in grape coloration was examined (Table 15). Addition of Latron B-1956 increased the percent clusters with color for ABA at 100 or 200 ppm after application and increased the harvest yield percent with sufficient color. ABA at 200 ppm with or without Latron B-1956 had more color and greater yield than at 100 ppm.

TABLE 15

Effect of Latron B-1956 on improving ABA performance in Crimson Seedless grape coloration.

| Treatment | Days after application (% clusters with color) | | | | | | | | Harvest yield (%) |
|---|---|---|---|---|---|---|---|---|---|
| | 21 | 27 | 35 | 43 | 50 | 56 | 62 | 64 | |
| Untreated control | 0.2 | 0.6 | 1.9 | 4.5 | 4.5 | 10.5 | 10.5 | 14.3 | 8.1 |
| ABA (100 ppm) | 1.8 | 2.7 | 5.7 | 7.5 | 9.4 | 26.1 | 26.2 | 31.2 | 25.5 |
| ABA (200 ppm) | 7.0 | 10.7 | 17.3 | 20.5 | 22.7 | 47.9 | 50.3 | 56.4 | 49.1 |
| Latron B-1956 (0.05%) + 100 ppm ABA | 4.6 | 5.5 | 15.1 | 18.5 | 21.6 | 48.1 | 48.9 | 54.5 | 47.9 |
| Latron B-1956 (0.05%) + 200 ppm ABA | 8.8 | 11.9 | 21.3 | 25.5 | 29.4 | 54.5 | 55.2 | 64.2 | 54.0 |

The invention claimed is:

1. An agricultural composition for enhancing and extending transpiration inhibition of abscisic acid (ABA) or salts thereof comprising from about 125 ppm to about 1000 ppm of ABA or salts thereof and from about 0.01% w/w to about 0.5% w/w of at least one surfactant selected from Brij 58, Brij 76, Brij 78, Brij 98, Agral 90, Latron B-1956 (a phthalic/glycol alkyl resin), and Monawet MO-84R2W.

2. The composition of claim 1 that further comprises a fertilizer.

3. The composition of claim 1 wherein the surfactant is selected from Brij 58, Brij 76, Brij 78, and Brij 98.

4. The composition of claim 3 wherein the surfactant is Brij 98.

5. The composition of claim 1 wherein the surfactant is Agral 90.

6. The composition of claim 1 wherein the surfactant is Latron B-1956.

7. The composition of claim 1 wherein the surfactant is Monawet MO-84R2W.

8. The composition of claim 2 wherein the fertilizer is a nitrogen-containing fertilizer selected from the group consisting of urea, ammonium nitrate and ammonium sulfate.

9. The composition in claim 8 wherein the fertilizer is urea.

* * * * *